United States Patent [19]

Turner

[11] Patent Number: 4,672,980
[45] Date of Patent: Jun. 16, 1987

[54] SYSTEM AND METHOD FOR CREATING HYPERTHERMIA IN TISSUE

[75] Inventor: Paul F. Turner, North Salt Lake, Utah

[73] Assignee: BSD Medical Corporation, Salt Lake City, Utah

[21] Appl. No.: 405,947

[22] Filed: Aug. 6, 1982

Related U.S. Application Data

[63] Continuation-in-part of Ser. No. 136,506, Apr. 2, 1980, Pat. No. 4,462,412.

[51] Int. Cl.⁴ .............................................. A61N 5/00
[52] U.S. Cl. ............................ 128/804; 219/10.55 R
[58] Field of Search ................... 128/804, 420 A, 399; 219/10.55 R, 10.55 B, 10.55 F, 10.81; 343/799

[56] References Cited

U.S. PATENT DOCUMENTS

| | | | |
|---|---|---|---|
| 2,582,806 | 1/1952 | Nes et al. | 219/10.81 |
| 3,095,880 | 7/1963 | Haagensen | 128/804 |
| 3,594,802 | 7/1971 | Koob | 343/799 |
| 4,148,321 | 4/1979 | Wyss et al. | 128/420 A |
| 4,271,848 | 6/1981 | Turner et al. | 128/804 |
| 4,397,313 | 8/1983 | Vaguine | 128/804 |
| 4,397,314 | 8/1983 | Vaguine | 128/804 |
| 4,434,341 | 2/1984 | Busby | 219/10.55 F X |
| 4,446,874 | 5/1984 | Vaguine | 128/804 |

FOREIGN PATENT DOCUMENTS

| | | | |
|---|---|---|---|
| 2420883 | 11/1975 | Fed. Rep. of Germany | 128/804 |
| 2941741 | 4/1981 | Fed. Rep. of Germany | 128/420 A |
| 1233947 | 10/1960 | France | 128/804 |

OTHER PUBLICATIONS

Guy et al, "Determination of Power Absorption...", IEEE Trans. Bio. Med. Eng., vol. BM-23, No. 5, pp. 361–371, Sep. 1976.

Magin, "A Microwave System... Animals", IEEE Trans.... MTT, vol. MTT-27, No. 1, Jan. 1979, pp. 78–83.

Primary Examiner—Lee S. Cohen
Attorney, Agent, or Firm—Hubbard, Thurman, Turner & Tucker

[57] ABSTRACT

A system and corresponding method for creating hyperthermia in target tissue has a computer control for applied electromagnetic radiation (EMR) in the HF, VHF and UHF microwave region. A real time thermal profile of the target and electric field readings provide feedback to the control. The frequency, amplitude, and relative phase of the EMR can be varied as necessary to create desired hyperthermia heating patterns in the target. The system utilizes controlled constructive interference between EMR emitted by several applicators in order to provide improved heating in the central regions of the target. Several different applicator arrays are suitable for use with the system, and comprise generally cylindrical annuli which emit radiation toward a central axis.

29 Claims, 11 Drawing Figures

SYSTEM AND METHOD FOR CREATING HYPERTHERMIA IN TISSUE

BACKGROUND AND SUMMARY OF THE INVENTION

The present application is a continuation-in-part of U.S. application Ser. No. 136,506, now U.S. Pat. No. 4,462,412 filed Apr. 2, 1980.

The present invention relates generally to systems and apparatus for irradiating targets with electromagnetic radiation, and more specifically to annular-type applicators and associated systems for controlling application of radiation to biological tissue.

Several types of therapeutic treatments for cancer in humans are in current, common use. These treatments include surgery, x-rays, radiation from radioactive sources and chemotherapy, these treatments being often combined in various ways to enhance treatment effectiveness.

Although such conventional treatment techniques have been successful in treating cancer in many patients and in prolonging the lives of many other patients, they are frequently ineffective against many types of cancer and often have severe adverse side effects at the necessary treatment levels. Protracted treatment of cancer patients by x-rays or chemotherapy, as an illustration, tends to eventually destroy or inhibit the patients' natural immunological systems to an extent that many patients eventually succumb to common infectious diseases, such as influenza or pneumonia, which otherwise probably would not be fatal. Also, many patients having advanced stages of cancer or complications may become too weak to withstand the trauma of surgical or other cancer treatments; hence, the treatments cannot be undertaken or must be discontinued.

Due both to the prevalence and the typically severe consequences of human cancer, as well as frequent ineffectiveness of current treatments such as those mentioned above, medical researchers are continually experimenting in an attempt to discover and develop improved or alternative cancer treatment methods with their associated treatment apparatus.

Hyperthermia, the generation of artificially elevated body temperatures, has recently been given serious scientific consideration as an alternative cancer treatment. Much research has been conducted into the effectiveness of hyperthermia alone or in combination with other treatment methods. This research is important in that hyperthermia techniques appear to have the potential for being extremely effective in the treatment of many or most types of human cancers, without the often severely adverse side effects associated with current cancer treatments.

Researchers into hyperthermia treatment of cancer have commonly reported that many types of malignant growths in humans can be thermally destroyed, usually with no serious adverse side effects, by heating the malignancies to temperatures slightly below that injurious to most normal, healthy cells. Furthermore, many types of malignant cell masses have reportedly been found to have substantially poorer than normal heat transfer or dissipation characteristics, presumably due to poorer vascularity and reduced blood flow characteristics. Consequently, these types of growths appear capable of preferential hyperthermia treatment. Poorly vascular malignant growths can reportedly be heated to temperatures several degrees higher than that in which the immediately surrounding healthy tissue reaches. This promises to enable hyperthermic treatment of those types of malignant growths which are no more thermally sensitive than normal tissue without destruction of normal cells, and additionally to enable higher temperature, shorter hyperthermia treatment times of more thermally sensitive types of malignancies which exhibit poor vascularity, usually an advantage for important medical reasons.

In this regard, researchers have commonly reported that as a consequence of these thermal characteristics of most malignant growths and the thermal sensitivity of normal body cells, hyperthermia temperatures for treatment of human cancer should be carefully limited within a relatively narrow effective and safe temperature range. Below a threshold temperature of about 41.5° C. (106.57° F.), significant thermal destruction of most malignant growths of cells has normally not been found to occur.

At slightly higher hyperthermic temperatures, above the approximate range of 43° C. to 45° C. (109.4° F. to 113° F.), thermal damage to most types of normal cells is routinely observed; thus, great care must be taken not to exceed these temperatures in healthy tissue. Exposure duration at any elevated temperature is, of course, an important factor in establishing extent of thermal damage to healthy tissue. However, if large or critical regions of the human body are heated into, or above the, 43° C. to 45° C. range, for even relatively short times, serious permanent injury or death may be expected to result.

Historically, alternating electric currents, at frequencies above about 10 KHz, were found late in the last century to penetrate and cause heating in biological tissue. As a result, high frequency electric currents, usually in the megahertz frequency range, have since been widely used for therapeutic treatment of such common bodily disorders as infected tissue and muscle injuries. Early in this century, the name "diathermia" was given to this EMR tissue heating technique, and several discrete EMR frequencies in the megahertz range have subsequently been allocated specifically for diathermy use in this country by the Federal Commerce Commission (FCC).

A number of even more current discussions relating to EMR hyperthermia treatment of cancer may, for example, be found in a compilation of articles on the subject published in the book "Cancer Therapy by Hyperthermia and Radiation", edited by Christian Streffer et al and published by Urban and Schwarzenberg; Baltimore, Munich 1978.

In spite of there having been reported encouraging and often apparently successful medical results obtained by using EMR induced hyperthermia to treat malignant growths in humans, the treatments have normally been of an experimental nature, typically being used on cancer patients otherwise considered incurable or terminal, since serious problems relating to hyperthermic damage to healthy tissue have commonly been encountered. As with conventional surface heating, these healthy tissue damage problems are particularly associated with thermally destroying malignant growths deeply located in, or close to, thermally sensitive tissue.

This unintended EMR thermal damage of healthy tissue can typically be attributed to design and use of existing EMR irradiating apparatus, rather than to any basic deficiency in the concept of EMR hyperthermia treatment. EMR apparatus used, for example, often radiate excessive and/or improperly controlled EMR heating fields. A further disadvantage is that the specific diathermy allocated frequencies which are ordinarily used are typically non-optimum radiating frequencies for deep penetration. In addition, existing EMR hyperthermia apparatus and techniques tend to increase incidence and severity of thermal "hot spotting" in healthy tissue, as may be caused by uncontrolled constructive interference of applied energy waves, either by characteristic reflections at interfaces between different types of tissue, or by simultaneous use of more than one EMR applicator.

To overcome these and other problems associated with heretofore available EMR hyperthermia apparatus used to medical research or other medical purposes, applicant has disclosed improved EMR hyperthermia apparatus in U.S. patent applications, Ser. No. 002,584, now U.S. Pat. No. 4,271,848, and 048,515, now U.S. Pat. No. 4,341,227, filed on Jan. 11, 1979 and June 14, 1979, respectively. In these two patent applications, parallel plate and waveguide-type EMR applicators, together with associated EMR systems, were described and claimed, the applicators being particularly adapted for irradiating biological tissue or tissue simulating matter from outside the tissue. Emphasis was placed on broad band EMR capabilities, enabling, for example, research definition of important parameters associated with hyperthermic treatment of malignancies in humans. Also described in such patent applications was simultaneous operation of two (or more) applicators arranged to improve deep tissue heating characteristics.

In applicant's subsequent U.S. patent application, Ser. No. 050,050, (continued as Ser. No. 305,180, now U.S. Pat. No. 4,448,198) filed on June 19, 1979 needle-type, invasive EMR applicators, for enabling EMR hyperthermia in sub-surface tissue regions, were described. By surrounding, with a phased array of these invasive applicators, a localized tissue region, such as a region containing a malignant growth, substantially uniform heating of the surrounded region by constructive interference of the synchronous EMR filed was described.

However, there still exists an important need for EMR hyperthermia apparatus capable of causing uniform deep EMR heating of thick tissue masses, such as trunk and thigh portions of an adult human body, in which large or widely dispersed malignant growths may be found. For these and similar regions of the body, an encircling annular EMR Applicator apparatus, which may comprise an array of smaller applicators, is ordinarily preferred so that EMR energy is emitted inwardly from all around the enclosed body region to be EMR heated.

To this end, large annular magnetic coils have been used to radiate a magnetic field into a body region disposed through the coil. Although such radiated magnetic fields are known to penetrate deeply in human tissue, uniform heating across the encircled tissue region is normally not possible. This has been reported by several researchers. This is because the induced currents couple much stronger in the longer current paths along the outer tissue regions than in the center. Thus, when such annular magnetic coils are used to cause hyperthermia in biological tissue, near surface tissue regions can be expected to be heated much more than underlying central tissue regions.

Presently available EMR applicators have failed to permit deep heating of a large target, such as a human torso, without severely damaging the overlying tissue. This is due to the lossy nature of biological tissue, which absorbs a certain fraction of EMR passing therethrough, such fraction being dependent on the tissue type and frequency of the EMR. Large amounts of the available power are absorbed near the surface, leaving relatively small amounts to be absorbed in the deeper regions. This causes excessive tissue heating at the surface, with little therapeutic heating in the desired location, which is the central region of the target.

Some heating improvement can be had in the central heating region by using several applicators surrounding the target. Such an array typically energizes the individual applicators at different frequencies, or frequencies which vary slightly with time, in order to avoid undesired hot regions caused by constructive interference between the different wavefronts. Such arrangements increase the power density in the central region to approximately the sum of the power densities due to the individual applicators without increasing appreciably the energy absorbed in a unit area of the target's surface. However, the power density in near-surface regions is usually still such as to be harmful to biological targets before heating reaches therapeutic values in the deeper regions.

When success in thermally treating deeply located malignant growths by heretofore available types of annular applicator apparatus has been experienced, the results appear to be more attributable to poorer heat dissipation properties of large malignant growths than to the desirable uniformity of heating. Heating uniformity, not heretofore available, would also enable effective thermal treatment, for example, of deeply located, widely dispersed, small groups of malignant cells in early stages of growth before the associated reduced heat transfer characteristics become significant. Ability to provide at least substantially uniform heating of encircled tissue regions is also very important, for example in areas of EMR hyperthermia research into hyperthermic effect on normal healthy tissue.

For these and other reasons, applicant has invented annular EMR applicator apparatus, and corresponding methods for EMR irradiation, which provide greatly improved uniformity of EMR heating in an encircled target, preferably of biological tissue or tissue simulating matter. Applicant's improved annular applicator apparatus provides such heating uniformity for whatever purposes the EMR heating may be required or desired, whether or not these purposes relate to medical hyperthermic treatment of cancer or of other medical research.

According to the present invention, an improved hyperthermia system utilizing electromagnetic radiation utilizes a computer control for real time monitoring and control of the system. A plurality of individual applicators are directed toward the central regions of the target. The amplitude and phase of energy supplied to each individual applicator is controlled by the system in order to meet the desired objectives. During operation, the system preferably monitors thermal and electric field distributions in and around the target. If the target is living vital signs are also preferably monitored. In the preferred embodiment, the information collected during system operation is compared with predicted thermal and electric field distributions which have previously been calculated and stored in memory. Phase, amplitude, and frequency of the energy supplied to the applicators are controlled by the system in order to provide optimum results and avoid medical complications.

The system can utilize different types of EMR applicators to heat the target. The preferred embodiment utilizes a device having a plurality of radiative applicators disposed in a cylindrical manner around the target. The relative phase and/or amplitude of energy to each applicator can be controlled as desired in order to provide the most useful heating patterns for use with the particular target. The individual applicators may be formed out of, for example, horn type radiators or dipole antennae.

The novel features which characterize the present invention are defined by the appended claims. The foregoing and other objects and advantages of the invention will hereinafter appear, and for purposes of illustration, but not of limitation, a preferred embodiment is shown in the accompanying drawings.

DESCRIPTION OF THE PREFERRED EMBODIMENTS

Figure 1:
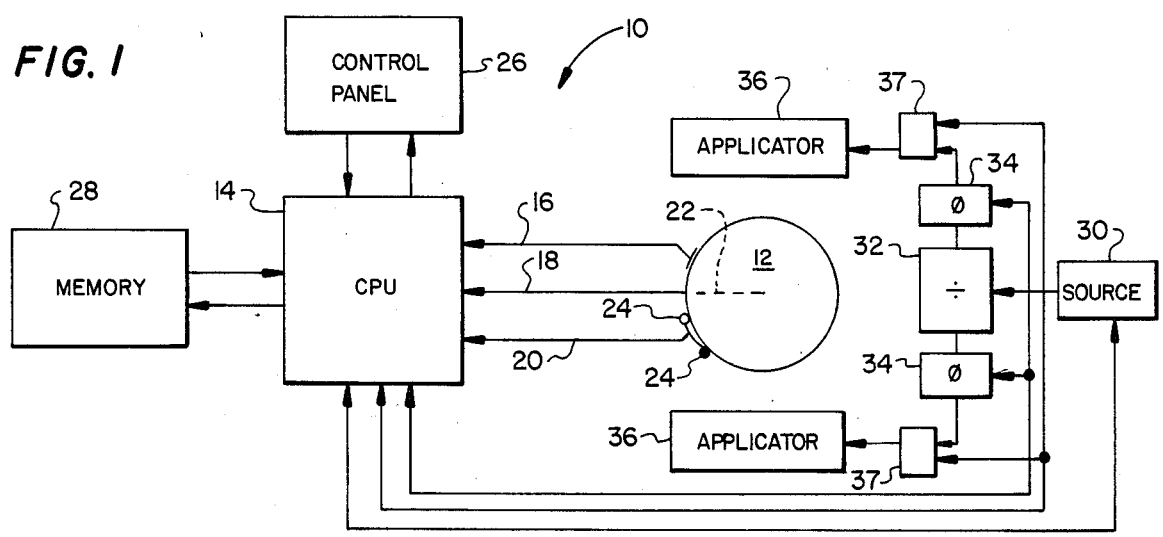
FIG. 1 is a schematic diagram of a system for creating hyperthermia in a target.

FIG. 1 shows a block diagram of a system 10 for creating hyperthermia in a target specimen 12 by means of electromagnetic radiation (EMR). A central processor unit 14 controls the system 10, and is in interactive feedback relationship with each of its elements. The central processor unit (CPU) 14 accepts a plurality of inputs describing the present condition of the target 12. These inputs can include, but are not necessarily limited to, signals relating to the target's vital signs 16, internal temperature distribution 18, and external electric-field distributions 20.

The vital signs input 16 is preferably for use with live targets 12. These signs can include, for example, mean arterial, diastolic, and systolic blood pressure, heart rate, oral temperature and other signs generally used by medical personnel to determine the overall status of a patient.

Figure 10:
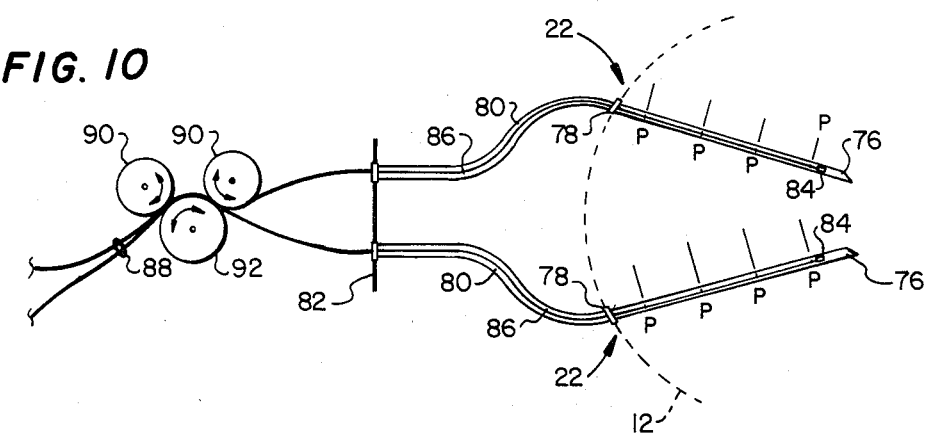
FIG. 10 is an idealized diagramatic view illustrating the operation of movable temperature probes for use with the system of the present invention.

The CPU 14 will also accept inputs 18 from a plurality of thermal probes 22, which is diagramatically shown in FIG. 1 as a single probe 22. These probes 22 give a real time indication of the internal temperatures within the target 12, and, when probes 22 of a type such as those described in connection with FIG. 10 are used, can give a either a two dimensional or three dimensional real time representation of thermal distributions within the target 12. This thermal information can be used to ensure that desired portions of the target 12 are heated to the proper temperature, and that no undesirable thermal gradients or concentrations occur.

The CPU 14 can also accept inputs 20 from electric field detectors 24 which indicate the real time electric field amplitude at selected locations. These detectors 24 are normally external of the target 12, and are preferably placed against or close to the surface. A plurality of E-field detectors 24 can be used, preferably at least 8, and these are represented diagramatically by a single input 20 to the CPU 14. These E-field detectors 24 provide feed-back to the CPU 14 of the relative amplitude balance of the EMR incidental to the target surface.

A control panel or console 26 is coupled to the CPU 14 and is used by an operator to control a treatment and monitor its progress. The control panel 26 can be used to display any information obtained from the target 12 as well as all indicators of system operation. Various memory devices, represented by a single memory block 28, are coupled to the CPU 14. The memory 28 stores the result of pretreatment calculations which are used by the CPU 14 to control the progress of the treatment. Also, all pertinent operating data are stored in another part of the memory 28 as generated in order to have a complete record of the treatment process and results for future use.

A high frequency energy source 30 is coupled to and controlled by the CPU 14. The source 30 is coupled to a power splitter 32, which divides energy into a plurality of lines each having the same phase and power. The phase of the energy in each line can be individually adjusted in a line stretcher 34. The output of each line stretcher 34 is coupled to one individual applicator 36. The actual delivery of power to the applicators 36 is controlled by switches 37 located between the line stretchers 34 and the applicators 36. The switches 37 may be simple on-off switches, such as relays or solid state switches, or they may be continuously variable. Like the source 30 and the phase shifters 34, the switches 37 are preferably controlled by the CPU during system operation, although the switches 37 may be manually operated. FIG. 1 shows only two line stretchers 34, applicators 36 and switches 37, but an actual system 10 typically employs at least four of each.

Figure 2:
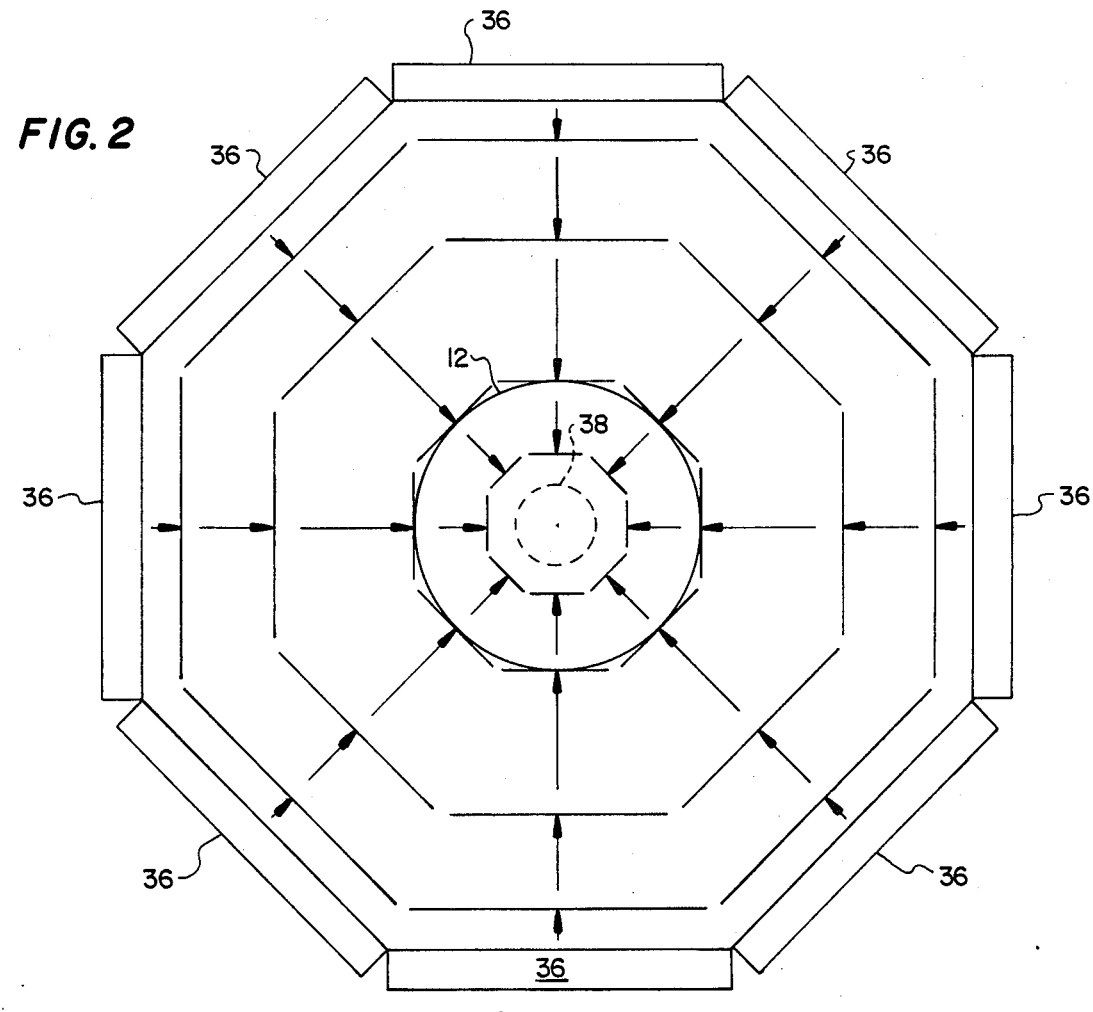
FIG. 2 is a diagram showing the method of operation of a system according to FIG. 1.

Referring to FIG. 2, eight individual applicators 36 are shown coupled together in an octagonal arrangement and surrounding a circular target 12. Each applicator 36 is diagramatically represented by a rectangle. In reality, each applicator 36 would have a shape suitable for the emission of microwave EMR, several embodiments of which are shown in later drawings. FIG. 2 is a two-dimensional representation of a three-dimensional phenomena, with both the radiators 36 and target 12 extending for some distance perpendicular to the plane of the drawing. The radiation emitted from each applicator 36 is aligned so that the electric field component is perpendicular to the plane of the drawing and the magnetic field component lies in the plane of the drawing. The stylized wave fronts shown in FIG. 2 approximate the geometry of the magnetic field component of EMR emitted by the various applicators.

As the radiation emitted by the various applicators 36 converges on the target 12, it is seen that the electric fields of the radiation are lined up so that the target 12 sees, approximately, a converging circular wave front. The energy of the various wave fronts converges in the center of the target 12, where the electric field adds constructively and heats the center regions 38 of the target 12 to a greater degree than that caused by any one of the applicators 36 alone. This improved deep internal heating is caused without dangerously increasing the radiant energy density at the surface of the target 12, as the incoming energy is normally spread equally over the entire target surface. Thus, the energy imparted to the target 12 is concentrated near the center, where it is desired, and minimized to the extent possible at the target surface.

As described in connection with FIG. 1, the energy radiated by each applicator 36 has a constant phase relationship with that emitted by the other applicators 36. This creates a synergistic result in the center area 38 of the target 12, whereby the target 12 is heated to a degree greater than that of a simple sum of the energy of the various applicators 36. The synergistic result will be described in more detail with relation to FIGS. 3 and 4. With all of the applicators 36 operating precisely in phase, the central heating area 38 will be symmetrical around the center point of a homogeneous target 12. If the shape or location of the control heating region 38 is desired to be other than symmetrical about the center, changing the relative phase of the EMR emitted by the various applicators slightly will cause the central heating region 38 to move generally toward the applicators 36 which are phase-lagging the remainder. By controlling the phase of energy emitted by the applicators 36 as described in connection with FIG. 1, it is therefore possible to manipulate the location of the central heating region 38 to best achieve the desired result. Manipulation of the central heating region 38 can also be accomplished through control of the switches 37. The power to each applicator 36 can be controlled as desired, through either on-off switches or continuously variable switches as described above. Lowering or cutting off power to individual applicators 36 changes the shape of the central heating region 38, and the power absorbed at various points in the target 12.

Figure 3:
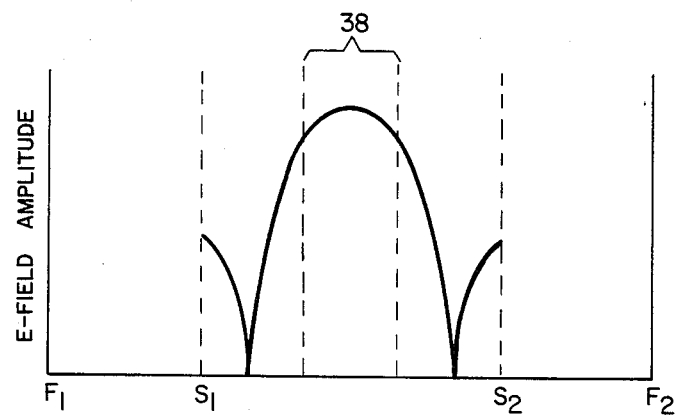
FIG. 3 is a diagram showing relative electric-field amplitudes within a homogeneous target specimen.
Figure 4:
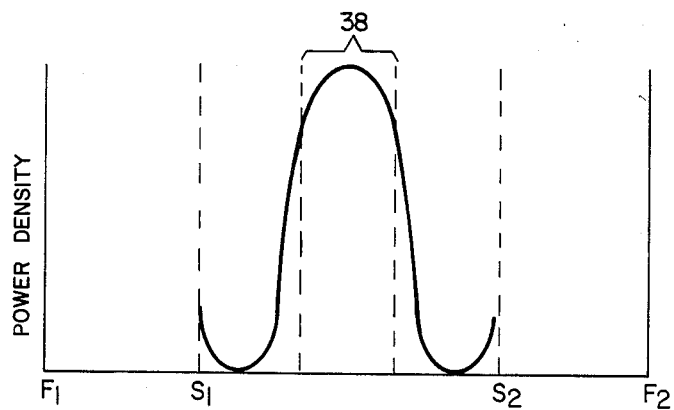
FIG. 4 is a diagram showing relative power density in a homogeneous target specimen.

FIGS. 3 and 4 show the mechanism by which the greatly increased power deposition in the central heating region 38 occurs. Considering any pair of diametrically opposed applicators 36 of FIG. 2, and a non-lossy homogeneous target 12, the drawing of FIG. 3 shows the standing wave amplitudes of the E-field component of the EMR generated by such opposing pair on a line through the center of the target 12. The horizontal axis represents the distance between the opposing applicator emission faces, shown as points $F_1$ and $F_2$, and the vertical axis represents the amplitude of the alternating E-field standing wave at each distance. The points $S_1$ and $S_2$ represent the opposite surfaces of the target 12 with no consideration presently being made of the E-field external to the target 12.

Because the two oncoming wave fronts are of identical frequency and have their E-fields aligned parallel to the center axis of the target 12, the electric field at each point between the applicators is the sum of the E-field vectors of each wave. When the frequency of the emitted radiation is chosen so that the wave length in the target 12 is approximately three-fourths the diameter of the target 12, the amplitude of the standing wave caused by two applicators 36 in the target 12 is shown in FIG. 3. The maximum amplitude is located in the center region 38, with minimums being located one-fourth wave length to either side of the center. The amplitude at the center is the sum of the maximum amplitudes from each applicator 36, which for the two opposed apertures is twice the E-field created by a single applicator 36. When more than two applicators 36 are used, as shown in FIG. 2 for example, the resultant E-field sum is of course larger.

Testing has shown that best results are normally obtained when the wavelength of emitted EMR is between approximately ¾ and twice the target 12 diameter. This gives a relatively well-defined central heating region 38 and a good impedance match between the applicators 36 as described below and the target 12. Thus, for a target 12 diameter d, the preferred range of wavelengths can be found from the expression:

$$0.5\lambda_m \leq d \leq 1.3\lambda_m \tag{1}$$

where $\lambda_m$ is the wavelength in the tissue medium being heated. For high water content tissues, such as muscle and blood, the wavelengths at 100, 300 and 915 MHz are approximately 27, 11.9 and 4.5 cm respectively. For low water content tissues, the respective wavelengths at the frequencies are approximately 106, 41 and 13.7 cm. If both types of tissue are present in a target, it is preferable to select a wavelength which satisfies equation (1) for the most prevalent tissue type (normally muscle tissue). A wavelength larger than suggested by equation 1 can be used if adequate impedance matching is obtained or provided by external matching techniques.

FIG. 4 shows the relative power density at each point in the target 12 corresponding to FIG. 3. The power density is proportional to the square of the electric field strength, so that the power density curve shows a relatively sharp peak in the central heating region 38 for a non-attenuating medium. Heating at any point is due to the power absorbed at that point, which is in turn directly proportional to the power density at that point. Therefore, a heating cross section of the target has the same distribution as the power density curve of FIG. 4 when heat transfer effects are neglected. However, a medium capable of absorbing the radiant power is attenuating and will substantially reduce the central power density peak as represented in FIGS. 3 and 4 and increase the power density somewhat at the surface.

Since the power density is proportional to the square of the E-field, a simple additive increase in the electric field at a given point results in an increase in the power density at that point by the square of the electric field. For example, in FIGS. 3 and 4 the electric field in the central heating region 38 resulting from 2 apertures is twice that due to a single applicator 36. Therefore, the power density of the central region is $2^2=4$ times the power density that would be caused by a single applicator 36. When, as in FIG. 2, more applicators 36 are used, the increase in power density becomes much greater than that caused by a single applicator 36. When eight applicators 36 are used, the E-field at the center is 8 times that caused by a single applicator 36 alone, and the power density at the center is therefore $8^2=64$ times the power density caused by a single applicator 36. This enormous increase in power density, and thus power absorbed, in the center of the target 12 is obtained without significantly increasing the power density at any one point on the surface of the target 12. This phenomena, a synergistic result due to all applicators 36 operating at the identical frequency and with a predetermined phase relationship, allows deep heating of the target 12 without undesired heating of the surface portions.

The above discussion of FIGS. 3 and 4 applies to non-lossy targets 12. In such targets 12 there is no energy absorption by the medium, so that the amplitude of the EMR from any given applicator 36 is undiminished as the radiation passes through. However, actual targets 12 are lossy, so that the amplitude of EMR decreases as it passed through the target 12. In a typical case, the amplitude of the E-field at the center region 38 may be approximately 1/7 the E-field amplitude at the surface of the target 12. For the case of eight applicators 36, the power density in the center region 38 is approximately $8^2/7^2$ or approximately 1.3 times that at the surface of the target 12. It is important to note, however, that the power density in the center region 12 is still sixty-four times that which would be caused by a single applicator 36 alone. The general shape of the E-field and power density wave forms of FIGS. 3 and 4 still apply, with the actual peak value in the center region 38 being diminished with a lossy medium.

The above-described synergistic increase in power density in the central heating region 38 occurs only when all applicators 36 radiate at the same frequency with the E-fields of the emitted EMR aligned. This E-field in phase alignment preferably occurs along the central axis of the target 12, which is perpendicular to the page as shown in FIG. 2. The E-field alignment of the various applicators 36 is preferably made as accurate as possible. However, some misalignment can be tolerated without unreasonably reducing the performance of the system 10. The vector sum of the E-field at any one point is equal to the sum of the individual E-field vectors. If a particular applicator 36 is misaligned, the EMR emitted by that applicator contributes to the synergistic power increase only in an amount proportional to the cosine of the angle between the misaligned E-field and the remaining E-fields. For small angles the cosine is close to one, so that small mismatches in the E-field alignment do not substantially degrade the synergistic power density enhancement which occurs in the central heating region 38.

When the various applicators 36 radiate energy at slightly different frequencies, it will become apparent to those skilled in the art that the various E-fields will not always add constructively, and the power density enhancement described above will not occur. In fact, in such a case, the power density in the central region 38 will be, at best, the simple sum of the individual power densities. It is therefore important that the frquency of radiation emitted by all applicators 36 be absolutely identical. For this reason, the preferred embodiment utilizes a single power source 30 and a power splitter 32 whereby the powr supplied to each applicator 36 has the same frequency. While it is possible to use multiple sources providing that they can be precisely phase locked to emit identical frequencies, the practical considerations to accomplish this would complicate the system and add expense with little benefit, thus the preferred configuration requires only a single source 30 and splitter 32. It is not necessary that the frequency supplied to the applicators 36 be invariant with respect to time. In fact, it is desirable that the source 30 have a controllable frequency so that it may be adjusted to optimize performance with various target 12 materials as described above.

The shape and location of the central heating region 38 is determined by the distribution of applicators 36 in operation, the relative phase between them, and the EMR frequency. It has been determined that the use of four or more uniformly spaced radiating applicators 36 will provide an approximately circular (ellipsoidal in three dimensions) central heating region 38. Eight radiating applicators 36 are used in FIG. 2 instead of four, because it has been determined that the power density, and thus heating, at the surface of the target 12 is more uniform than when only four radiating applicators 36 are used. An increase in the number of applicators 36 above eight does not appear to make a material difference in the operation of the system 10.

When all of the applicators 36 are precisely in phase, a symmetrical heating region 38 is formed in the precise center of a homogeneous target 12. Varying the relative phase of energy emitted by the various applicators 36 will cause the central heating region 38 to be shifted somewhat away from center toward the applicators 36 with lagging phase. The ability to alter the relative phase and amplitude between the applicators 36 is extremely useful, for example when a non-homogeneous target 12 (such as an animal torso) is used. The wavelength of the EMR will vary slightly in the different tissues of the target 12, and an alteration in emitted phase can compensate for the phase shifts thereby induced. Thus, when the target 12 has a known cross section of different tissues having known properties, the phase between the various applicators 36 can be adjusted to position the central heating region 38 at the desired location.

Figure 5:
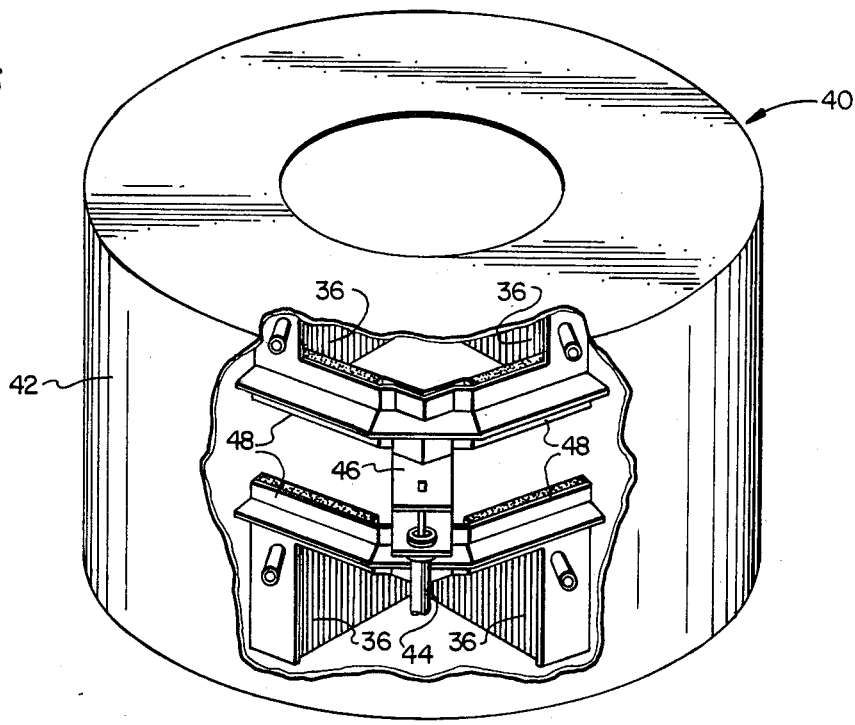
FIG. 5 is a partially cut away perspective view of one preferred applicator for use with the present invention.
Figure 6:
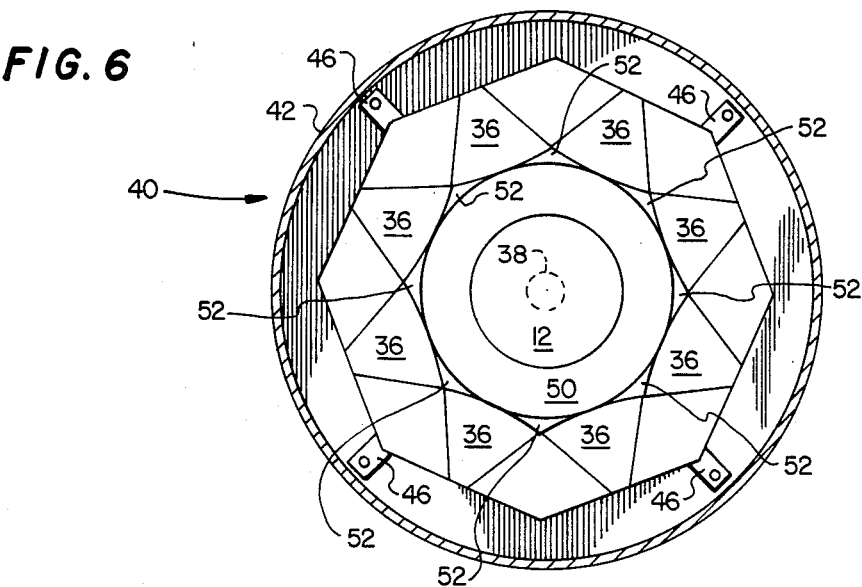
FIG. 6 is a top diagramatic view showing operation of the applicator of FIG. 5.

One applicator array 40 suitable for use with the present invention is shown in FIGS. 5 and 6. This annular array 40 comprises a battery of sixteen horn-type parallel plate waveguide antennae forming a folded dipole array being coupled together into two layers of eight radiators 36 each. For simplicity in construction, each input to the applicator array 40 feeds a two by two array of individual applicators 36. Thus, only four power inputs are needed for this sixteen applicator array 40.

It has been determined that the stacking of two or more applicators 36 in the E-field direction (perpendicular to the page in FIG. 2) still provides a substantially uniform electric field vertically but reduces the applicator size. It has also been determined that stacking of the individual applicators 36 in an annular array 40 along the H-field (in the plane of the page in FIG. 2) provides a substantially uniform electric field around a target 12. Use of an array of individual applicators 36 allows each one to be sized and constructed so as to provide a good impedance match between the applicators 36 and the target 12. A detailed discussion of methods for fabricating horn-type applicators 36 suitable for use with the present invention is contained in pending U.S. patent application Ser. No. 136,506, filed on Apr. 2, 1980, and titled Annular Electromagnetic Radiation Applicator For Biological Tissue And Method, which disclosure is herein incorporated as if set forth verbatim.

The applicator array 40 is surrounded by a casing 42, which serves to support the individual applicators 36 in place and to decrease stray radiation, which can be hazardous. As shown in FIG. 5, the casing 42 is partially cut away, exposing portions of four separate applicators 36. A coaxial power input line 44 is coupled to a parallel plate waveguide 46. The waveguide 46 is coupled to four feed guides 48. The feed guides 48 are in turn coupled to four individual applicators 36, and have the same dimensions so that power is split evenly to the applicators 36. Each set of four applicators 36 therefore radiates energy having the same phase, power and E-field alignment.

FIG. 6 shows a top view of the applicator array 40. A target 12 is suspended interiorly of the array 40, and is surrounded by a bolus 50. The bolus 50 preferably contains deionized water, and is made from a flexible material so as to seal tightly around the target 12. Air gaps 52 may be left between portions of the bolus 50 and applicators 36, or the bolus may be manipulated to fill these gaps as desired.

The use of a bolus 50 has several important advantages. The fluid therein can be circulated through an external heat exchanger (not shown) to cool surface regions of the target 12. When deionized water is used in the bolus 50, there is very little power loss in the bolus 50, so that the full power radiated by the applicators 36 is delivered to the target 12.

Use of the bolus 50 improves the impedance match between the applicators 36 and the target 12. At the frequencies of interest, the impedance of a typical biological target 12 is approximately 44 ohms. The impedance of the applicators 36 and other electrical portions of the system is preferably 50 ohms in order to be compatible with standard components. The impedance of deionized water at the frequencies of interest is also approximately 44 ohms, so that all parts of the system 10 are inherently closely matched. If the water-filled bolus 50 were not present, a large mismatch would occur at the radiating face of the applicators 36 and at the surface of the target 12. This mismatch occurs because the impedance of air is approximately that of free space, or 377 ohms. Any impedance mismatches cause reflections at the boundaries, lowering the percentage of radiated energy delivered to the target 12 and increasing stray radiation hazards.

As can be seen in FIG. 6, the applicator array 40 emits energy in the pattern discussed hereinbefore in connection with FIGS. 2 and 3, resulting in the power density pattern shown in FIG. 4. Thus, the applicator array 40 provides heating in the central region 38 without damage to the surface regions.

Figure 7:
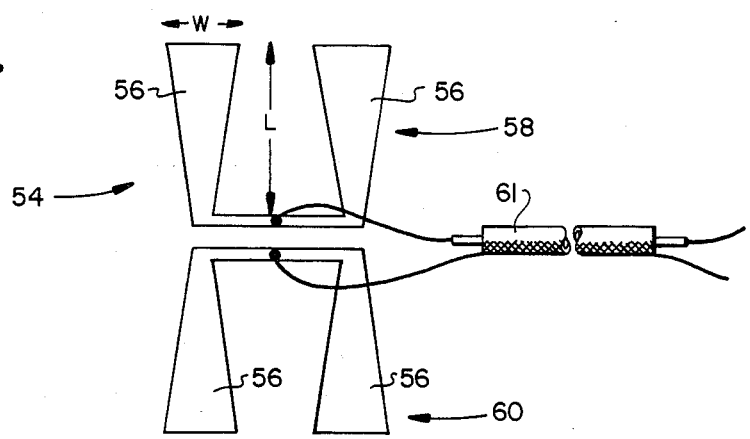
FIG. 7 is a diagram of a dipole antenna for use with the present invention.

An alternate embodiment of an applicator suitable for use with the present system 10 is shown in FIG. 7. This applicator 54 is essentially a dipole antenna pair sized for use with EMR of the frequencies contemplated. Each arm 56 of the upper and lower radiating portions 58,60 acts as a single radiator in a manner similar to that of the annular array 40 of FIGS. 5 and 6. A coaxial feed line 61 is coupled to the center of the upper and lower radiating portions 58,60. When this applicator 54 is driven in a conventional manner, the E-field of the emitted radiation is aligned with the length of the arms 56.

The shape and size of the antenna arms 56 determine the optimum frequencies of operation and impedance characteristics of the dipole 54. It has been determined experimentally that a dipole 54 having tapered arms, wherein the ratio of arm width (W) to length (L) is maintained constant at approximately 0.087, gives a good impedance match with remainder of the system 10. When the dipole applicators 54 are combined into a cylindrical array 66 as shown in FIG. 8, and a water bolus (not shown) as similar to that discussed with FIG. 6 is used, a reasonably good 50 ohm impedance match is achieved.

Figure 8:
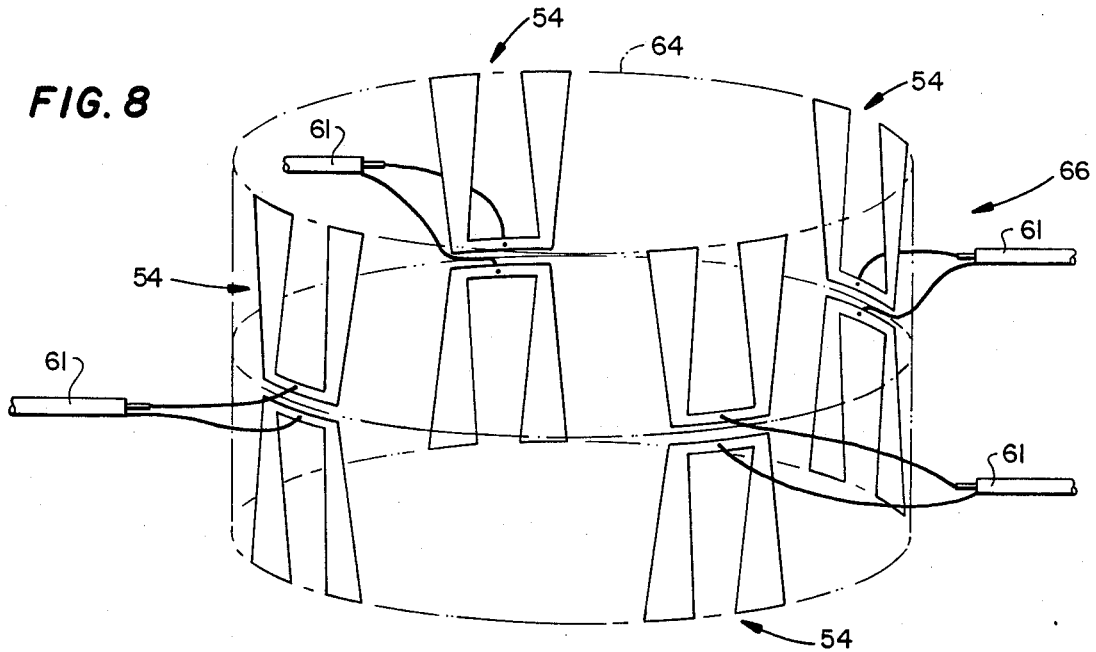
FIG. 8 is a perspective view of a folded dipole array for use with the system of the present invention.

Referring to FIG. 8, four dipole pair radiators 54 are assembled on a rigid, non-conducting frame 64 to form a cylindrical array 66. Each dipole radiator 54 is separately connected to the source 30 and power splitter 32 through a separate coaxial feed line 61. Each applicator 54 launches microwave EMR towards the center of the array 66 where the target specimen (not shown) is located. Preferably, a de-ionized water bolus (not shown) surrounds the target so as to better couple energy from the applicators 54 to the target, and to minimize reflections. The phase of the energy to each dipole applicator 54 can be controlled to vary the location of the central heating region 38 or to compensate for wavelength variations in non-homogeneous targets as described in connection with FIG. 2.

Figure 9:
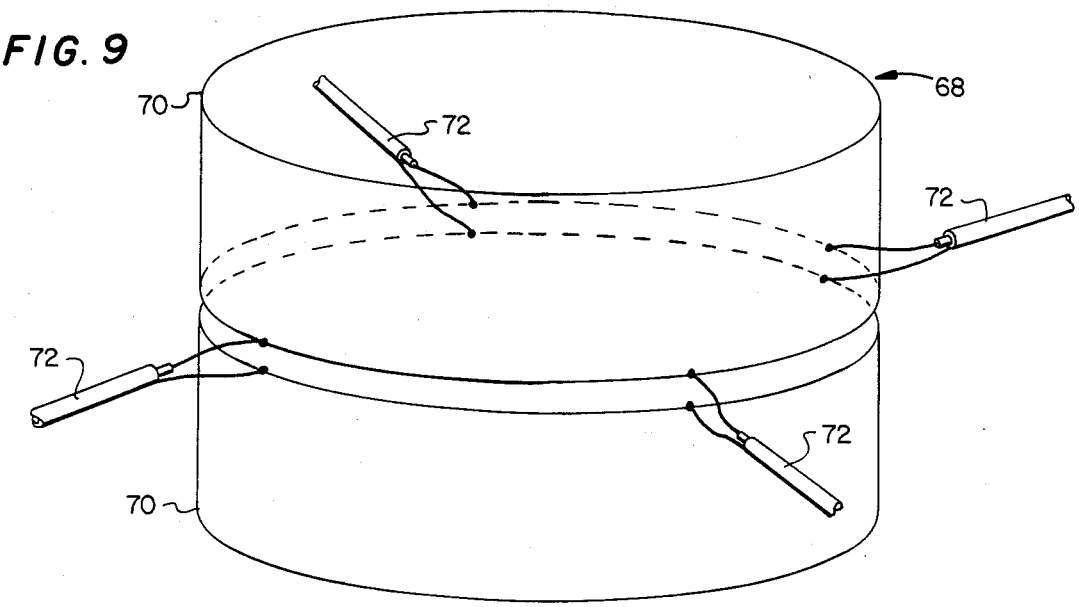
FIG. 9 is a perspective view of a third preferred applicator for use with the present invention.

Referring to the alternate embodiment of FIG. 9, a cylindrical dipole applicator 68 comprises two coaxial conducting cylinders 70 placed close together. These concentric cylinders 70 act as a single dipole applicator wherein the radiating arms comprise a flat radiating sheet which has been folded around to make contact with itself. The cylindrical dipole 68 will radiate toward its central axis, and constructive interference of the E-field will cause the synergistically increased power absorption in the central region 38 as described with the previous applicators. A single coaxial feedline 72 is sufficient to drive the cylindrical dipole 68. However, there will be some phase lag in the EMR emitted from the portions of the dipole 68 diametrically opposite the feedline 72. This will cause the central heating region 38 to shift somewhat away from the feedline 72 contacts. While this may be desirable in some cases, the preferred embodiment includes four coaxial feedlines 72 equally spaced around the dipole 68. When all four feedlines 72 are driven at the same phase, the central heating region 38 will be centered around the axis of the cylindrical dipole 68. Some manipulation of the central heating region 38 location can be made by varying the phase to the coaxial feed lines 72, lbut in general the degree of control will be less than that experienced with either the dipole array 66 or the horn radiator array 40.

Since the effective radiating aperture width of the cylindrical dipole 68 is equal to its circumference, and the height is limited by the size of the target to typically two feet or less, inherent impedance matching as was obtained with the dipole array 66 is difficult to achieve. Since the cylindrical dipole radiator 68 will not be inherently matched with the impedance of the remainder of the system at most desirable frequencies, a conventional impedance matching device (not shown) should be used to minimize losses and reduce reflected power.

Both the folded dipole array 62 and the cylindrical dipole 68 emit radiation from both their inner and outer surfaces. An internal water bolus will increase the proportion of radiation emitted centrally, due to the better impedance match. In order to reduce further the hazard of stray radiation, an outer conducting cylinder (not shown) can be placed around the cylindrical dipole 68 or dipole array 66. This outer shield can be grounded or left floating in order to reflect such radiation and reduce the outwardly emitted radiation. The reflecting shield must be spaced a sufficient distance from the cylindrical dipole 68 or dipole array 66 so that the ground plate will not capacitively load the aperture so much as to interfere with the primary emitted radiation distribution and reduce heating in the central region 38 or cause undesired non-central heating. In the preferred embodiment, the outer conducting cylinder is grounded and displaced so that minimal power pattern changes occur. Normally the space between the outer cylinder and the dipoles is filled with air or another low dielectric material thereby reducing the amount of energy coupled to the shorting cylinder. The grounding of the outer conducting cylinder is preferably done with a second coaxial outer shield dielectrically spaced from and outside of the coaxial outer conductor connecting to the dipole radiators.

In order to provide an effective hyperthermia treatment, the operator must be able to accurately determine the internal status of the target 12. For a living target 12, monitoring the vital signs gives a general indication of the health of the target 12 and indicates adverse events affecting its health. However, these signs, such as pulse, respiration, blood pressure and oral temperature, do not indicate whether enough heat is being applied to the region of interest to be effective.

Two additional measurements provide a fairly complete picture of the internal local effects of the hyperthermia treatment. The first of these is the measurement of actual temperature at selected points within the target 12. A real time thermal profile allows the operator to determine whether the desired regions of the target 12 are being heated to temperatures which are medically effective. Such a profile also allows the operator to ensure that no unwanted heating occurs in undesired portions of the target 12.

Referring to FIG. 10, a means for generating a thermal map of the target's interior is shown diagramatically. Two individual probes 22 are shown, although four to eight are commonly used when the system 10 is in operation. The probes 22 are invasively placed in the target 12. Catheters 76 are initially inserted into the target 12 in a predetermined location. The catheters 76 have closed tips so that no fluids from the target 12 flow into the catheter 76. The catheters 76 have surface indicating guides 78 which are pressed flush with the surface of the target 12 to ensure proper positioning. Coupled to the catheter 76 at the surface guide 78 is a flexible but fairly stiff hollow tube 80. This hollow tube or casing 80 is firmly coupled to a solid mounting plate 82.

A thermal sensor 84 is located inside the catheter 76. Such sensor 84 is preferably a non-metallic high resistance sensor, and should be of a type which will not affect or be affected by incident microwave radiation. The sensor 84 must reflect the true transparent in the region of its placement and should be free of distortion from the microwave radiation which falls upon it. Sensor leads 86 have a high electrical resistance so as to be unaffected by the electromagnetic field, and are wrapped in a dielectric material so as to form a single stiff but somewhat flexible lead 86. In the alternative, an optical thermal sensor 84 using fiber optic leads 86 may be used, as it is unaffected by microwave radiation. The leads 86 run through the catheter 76 and the casing 80, and pass through the fixed plate 82. The interior diameter of the casing 80 is slightly larger than the diameter of the stiffened lead 86 to allow longitudinal movement without binding.

Since the thermal sensor leads 86 are stiff, movement of such leads 86 will vary the position of the sensor 84 within the catheter 76. This allows temperature measurements to be made at several positions along the catheter 76 during operation of the system 10, thus maximizing thermal gradient information while minimizing the number of invasive devices required.

The probe leads 86 pass through the plate 82, and are coupled together by a collar 88. Two capstan rollers 90 keep the leads firmly in contact with a sheave 92, which in turn is driven by a stepping motor (not shown) or other means which allows the position of the leads 86 to be precisely determined. This precisely determines the position of the various temperature sensors 84. As shown in FIG. 10, four measurement positions P for the sensors 84 correspond with four predetermined sheave 92 positions.

During operation of the system 10, the CPU 14 is programmed to record data, taken by the thermal sensors 84, in the memory 28. The position of the stepping motor is controlled by the CPU 14, and the sensors 84 may be positioned in a predetermined measurement sequence, or a special sequence if the operator determines that an anomaly appears to be present and desires specific readings pertaining thereto.

The central processor 14 causes the thermal information taken during operation of the system 10 to be stored in long-term memory (e.g., disk) for later analysis. The system 10 also uses this information in a feedback loop to control the operation of the power source 30 and splitter 32. If heating should rise to dangerous levels, the power applied to the target 12 can be decreased. Likewise, if the heating is insufficient, extra power can be applied. The CPU 14 can also display a temperature vs position plot of several of these scanning sensors 84 for the operators to view.

In addition to the real time thermal condition of the target 12, information describing the real time power absorption patterns by the various tissues can be supplied by the present system 10. The power absorbed by a given region of tissue is directly proportional to the power density in that region. As discussed in connection with FIGS. 3 and 4, the power density is proportional to the local electric field of the microwave radiation emitted by the applicators 36. In a non-homogeneous target 12 such as a biological specimen, the power density in a particular tissue is also proportional to the conductivity of that tissue.

When the system 10 is used to generate hyperthermia in a human torso, it is preferable to gtake a computerized axial tomographic (CAT) scan of the regions to be heated. The results of the CAT scan are reduced to a two or three dimensional model suitable for computer processing. The model consists of a relatively large number of small "cells", or regions. For example, 20–50 cells may be used to model a human heart.

Each cell consists of only one tissue type, and is assigned the known properties ascribed to that tissue type. For example, at frequencies in the approximate range of 50–900 MHz, high water content tissues such as muscle and blood have a real part of permittivity approximately 50–90 times that of air, and a conductivity in mhos/meter in the region of 0.6–1.5. Precise values depend on the precise tissue type. Deionized water has a real permittivity of approximately 80 times that of air and a conductivity of zero. The close match in permittivity causes good impedance matching with high water content tissues and the zero conductivity ensures no power loss by EMR passing through, which are among the reasons a water bolus 50 surrounding the target 12 is preferred as described above.

Low water content tissues such as fat and bone have real permittivities and conductivities much lower than high water content tissues, so that power absorbed by these tissues is much lower for the same applied E-field than for high water content tissues. Use of both the real part of permittivity and conductivity is necessary to model the target 12. Experience has shown that by initially assuming that the target 12 is represented by an equivalent homogeneous media the calculations can be simplified, giving a good approximation of the E-field distributions in the target 12. The conductivity of each cell is then used to predict the estimated power density by Ohm's law.

Given a model of the target 12 to be heated, and the properties of the various tissues encountered, predictions are made of the power absorption patterns expected with the application of EMR. The prediction functions assume that each cell is homogeneous, and use conventional iterative methods to arrive at a solution. Solutions are calculated for a range of frequencies, amplitude, and phase relationships between the applicators 36. For each operating situation, first the E-field solution is generated, followed by the corresponding power density solution. The solution templates are stored in the system memory 28 for reference and comparison by the CPU 14 during operation of the system 10.

It is theoretically possible to have the CPU 14 generate the appropriate solutions during system 10 operation. However, solving the model for various operating conditions consumes enormous amounts of processor time given the present state of the art, which would not allow the system 10 to operate in real time. By generating solution templates in advance, the CPU 14 can quickly scan for the predicted solution that most closely matches known conditions. The frequency, amplitude, and phase of emitted radiation can be controlled as necessary in order to provide the desired power density patterns.

If the heat transfer characteristics of the target 12 are known, temperature distribution templates can also be generated in advance. Due to the complexity of blood flow and heat transfer in biological systems, it is not presently possible to accurately predict temperature distribution patterns in living biological targets 12 generally. However, after several hyperthermia sessions have been undergone with a particular target or class of targets, the stored results allow better estimates of heat transfer patterns. Also, the system 10 monitors the real time temperature distributions, and is able to compensate for unforeseen imbalances.

As described above, the power density in a region is proportional to the E-field squared and the tissue conductivity. Since the spatial distribution of tissue types is known from the CAT scan, measurement of the E-fields in various locations determines the power density. For a given target 12, a given E-field distribution external of the target 12 under known operating conditions (frequency, phase, specimen location, and so forth) implies a unique internal E-field distribution. By measuring the E-field distribution near the surface of the target 12, and matching these values with the closest prediction template, the E-fields within the target 12 can be determined without the necessity for invasive measuring devices.

Figure 11:
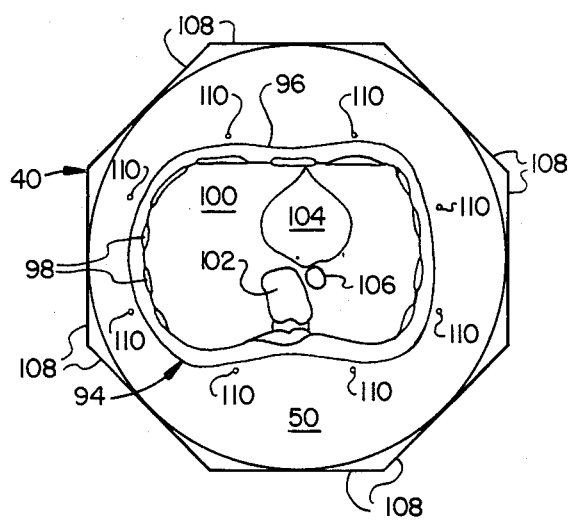
FIG. 11 is a cross section of an idealized torso used as a target specimen in conjunction with the system of the present invention, showing the location of electric field detectors.

Referring to FIG. 11, a cross-section of a human torso 94 is shown located within an annular array 40 of the type described in FIGS. 5 and 6. The simplified cross-section of the torso 94 consists of a chest wall 96, ribs 98, lung tissue 100, spine 102, heart 104 and a major artery 106. A bolus 50, preferably containing deionized water, surrounds the torso 94 and fills the space between it and the radiating surfaces 108. Located adjacent to the torso 94 are a plurality of E-field detectors 110. These detectors 110 are semiconductor diode detectors which do not distort the electric field which they are measuring. Since the E-field of the radiation emitted by all of the radiating surfaces 108 is parallel, and perpendicular to the page of the drawing, the E-field detectors 110 are also aligned perpendicular to the page of the drawing. For simplicity and accuracy in placement of the detectors 110, they may be coupled to the bolus 50 adjacent to the torso 94. The external E-field amplitudes as measured by these detectors 110 allow determination of the internal E-field and power density distributions as described above.

Although a preferred embodiment has been described in detail, it should be understood that various substitutions, alternations, and modifications may become apparent to those skilled in the art. These changes may be made without departing from the spirit and scope of the invention as defined by the appended claims.

What is claimed is:

1. A system for heating a target with electromagnetic radiation, comprising:

a control unit;

a power source coupled to said control unit, wherein the output frequency of said source is determined by said control unit;

a power splitter coupled to said source and having a plurality of outputs, wherein the energy supplied to each output is supplied simultaneously and has the same phase and power;

a plurality of individual applicators for radiating electromagnetic energy into the target wherein the electric field of the energy from each applicator is aligned with a common axis so that the electric fields of the respective applicators can overlap in a central region of said target to provide summation of the electric field energy within the central region for enhanced heating of the target;

a plurality of phase shifters coupled to the outputs of said splitter and to said control unit, wherein the phase of energy available at outputs of said phase shifters is determined by said control unit;

a plurality of switches coupled to the outputs of said phase shifters and to said applicators for controlling the amount of energy conveyed to said applicators;

at least one temperature probe coupled to said control unit and adapted for insertion into the target for indicating the temperature in selected regions of the target;

at least one electric field detector coupled to said control unit in the vicinity of the target for indicating the electric field strength in selected regions external of the taget, wherein the operation of said control unit varies as a function of the temperature and electric field indications;

memory means coupled to said control unit for storing data generated during operation of the system, and for storing data generated prior to system operation, wherein the prior generated data is compared to the operating data by said control unit during system operation; and means coupled to said control unit for displaying data generated during operation and for allowing an operator to control operation of the system.

2. The system of claim 1, wherein said applicators are coupled together into a generally cylindrical array, wherein said applicators radiate energy toward an axis of the array, and further wherein the array axis is substantially aligned with the common axis of electric field orientation.

3. The system of claim 1, wherein said at least one electric field detector comprises a semiconductor diode aligned with the common axis of electric field orientation.

4. The system of claim 1, wherein said temperature probe comprises:
   a hollow catheter adopted to be inserted into the target;
   a temperature sensor movably located inside said catheter; and
   means for positioning said sensor at a plurality of predetermined positions in said catheter.

5. A method for selectively heating a target, comprising the step of simultaneously irradiating the target with electromagnetic radiation from a plurality of dipole applicators, wherein the radiant energy from each applicator has the same frequency and aligned electric fields arranged parallel to the target, and there is predetermined phase relationship between the energy radiated by the applicators such that the electric field energy of the respective applicators overlaps sufficiently to provide enhanced heating of a central region of the target by summation of the electric fields.

6. A method for controllably heating a target to cause a temperature rise therein, comprising the steps of:
   (a) irradiating the target with electromagnetic radiation from a plurality of applicators surrounding the target, wherein the radiant energy from the applicators has the same frequency and aligned electric fields for increasing substantially the power density within a central region of the target for producing enhanced heating in the central region;
   (b) determining the power density distribution within the target during operation;
   (c) controlling the frequency of the radiation emitted by the applicators as a function of the results of step (b);
   (d) controlling the relative phase of the radiation emitted by the applicators as a function of the results of step (b);
   (e) controlling the power emitted by the applicators as a function of the results of step (b).

7. The method of claim 6, wherein step (b) comprises the steps of:
   (b1) determining the spatial arrangement of tissue types in the target;
   (b2) calculating predicted electric field distributions in and near the target for a range of operating conditions;
   (b3) storing the predicted distributions;
   (b4) measuring the electric field distributions external to the target;
   (b5) comparing the electric field measurements with the predicted electric field distributions;
   (b6) selecting the predicted electric field distribution which most closely matches the measured electric field distribution; and
   (b7) calculating the power density distribution based on the results of steps (b1) and (b6).

8. The method of claim 7, wherein steps (b1), (b2) and (b3) are performed prior to step (a).

9. The method of claim 6, wherein step (b) comprises the steps of:
   (b1) determining the spatial arrangement of tissue types in the target;
   (b2) calculating predicted electric field distributions in and near the target for a range of operating conditions;
   (b3) storing the predicted distributions;
   (b4) calculating predicted power density distributions based on the results of steps (b1) and (b3);
   (b5) measuring the electric field distributions external to the target;
   (b6) comparing the electric field measurements with the predicted electric field distributions;
   (b7) selecting the predicted electric field distribution which most closely matches the measured electric field distribution; and
   (b8) selecting the predicted power distribution corresponding to the electric field distribution selected in step (b7).

10. The method of claim 9, wherein steps (b1), (b2), (b3) and (b7) are performed prior to step (a).

11. The method of claim 6, further comprising the step of:
   (f) measuring the internal temperature distribution within the target during operation;
   wherein the controlling steps (c), (d) and (e) also operate as a function of the results of step (f).

12. The method of claim 11, wherein step (f) comprises the steps of:
   (f1) moving a temperature sensor along a catheter track to one of a plurality of preselected locations;
   (f2) measuring the internal target temperature at the preselected location with the temperature sensor; and
   (f3) repeating steps (f1) and (f2).

13. The method of claim 6, further comprising the step of:
   (f) storing, in a mass storage medium, measured, determined and controlled values generated during irradiation.

14. A system for heating a target with electromagnetic radiation, comprising:
   a central control unit;
   a source coupled to said control unit, wherein said source generates electromagnetic energy at a frequency and power determined by said control unit;
   means coupled to said source for transferring energy from said source to said target and including a plurality of individual applicators for simultaneously radiating energy into the target wherein the electric field of the radiated energy from each applicator is aligned with a common axis to provide summing of the electric field at a central region of said target, and the radiated energy has a wavelength related to the diameter of the target and further including a power splitter coupled to said source, wherein said splitter has a plurality of outputs each having the same phase and power, and including a plurality of phase shifters coupled to said splitter, to said applicators and to said control unit, wherein the phases of energy supplied to said individual applicators are controlled by said control unit; and
   means coupled to said control unit for indicating the status of the target, wherein operation of the system is controlled by said control unit as a function of the target status.

15. A system according to claim 14, further comprising means coupled to said phase shifters and to said applicators for controlling the power of the energy transferred to said applicators.

16. The system of claim 14, wherein said indicating means comprises at least one electric field probe for indicating the electric field in selected regions external to the target.

17. The system of claim 16, wherein said indicating means further comprises at least one temperature probe for determining the temperature in selected regions of the target.

18. The system of claim 17, further comprising a memory unit coupled to said control unit, wherein said memory unit includes data produced during the operation of the system and data produced in advance for comparison with the operation data.

19. The system of claim 18, further comprising a control and display means coupled to said control unit, wherein data produced during the operation of the system can be displayed in human readable form upon the display means and said control means receiving inputs from an operator for providing operational data to said control unit.

20. A system for heating a target with electromagnetic radiation, comprising:
a central control unit;
a source coupled to said control unit, wherein said source generates electromagnetic energy at a frequency and power determined by said control unit;
means coupled to said source for transferring energy from said source to the target and including a plurality of individual applicators for radiating energy in the target wherein the electric field of the radiated energy from each applicator is aligned with a common axis to provide summing of the electric fields for forming a central region of enhanced heating within the target, a power splitter coupled to the source, wherein said splitter has a plurality of outputs each having the same phase and power, and a plurality of phase shifters coupled to said splitter, to said applicators and to said control unit, wherein the phases of energy supplied to said individual applicators are controlled by the control unit, and further including means coupled to the phase shifters and to the applicators for controlling the power of the energy transferred to the applicators; and
means coupled to the control unit for indicating the status of the target, and including at least one electric field probe for indicating the electric field in selected regions external of the target, wherein the central control unit includes means for controlling the source of the system as a function of the indicated electric field to provide a predetermined heat pattern balance by regulating the electromagnetic energy generation.

21. The system of claim 20, wherein said indicating means further comprises at least one temperature probe for determining the temperature in selected regions of the target.

22. The system of claim 21, further comprising a memory unit coupled to said control unit for including data produced during the operation of the system and data produced in advance for comparison with the operation data.

23. The system of claim 22, further comprising an input and display means coupled to the control unit, said display means for displaying data produced during the operation to an operator and the input means for receiving input data from the operator for providing operational control data to said control unit.

24. A system for heating a target with electromagnetic radiation comprising:
a central control unit;
an electromagnetic source means connected to said central control unit for generating electromagnetic energy at a frequency and power determined by the control unit;
transfer means connected to the source means for transferring energy from the source means to the target; and
indicating means connected to the control unit for indicating the electric field in selected regions external of the target, wherein the central control unit includes means for controlling the source means as a function of the indicated electric field to provide a predetermined heat pattern balance by regulating the electromagnetic energy generation.

25. The system according to claim 24 wherein said indicating means includes at least one electric field probe.

26. The system of claim 24 wherein said transfer means includes a plurality of individual applicators for radiating energy into the tumor wherein the electric field of the radiated energy from each applicator is aligned with a common axis to provide summation of the electric fields at said tumor.

27. The system of claim 26 wherein said electromagnetic source means is a single source for applying electromagnetic energy simultaneously to each of said applicators.

28. The system of claim 24 wherein said transfer means includes a plurality of individual applicators and said electromagnetic source means is a single source for applying electromagnetic energy simultaneously to each of said applicators.

29. A method of an selectively heating a tumor imbedded within a living organism comprising the steps of:
(a) aligning a plurality of electric field applicators about at least a portion of said tumor to provide for aligned and electric fields providing energy to heat said tumor sufficient so that the electric field energy from the applicators can be summed;
(b) simultaneously applying electromagnetic energy to each of said applicators; and
(c) controlling the intensity and phase of the applied energy to each of said applicators to permit summing of the electric field energy at the tumor to enhance the heating thereof.

* * * * *